United States Patent [19]

Strutz

[11] Patent Number: 4,973,748
[45] Date of Patent: Nov. 27, 1990

[54] PROCESS FOR THE OLIGOMERIZATION OF HEXAFLUOROPROPENE OXIDE

[75] Inventor: Heinz Strutz, Frankfurt am Main, Fed. Rep. of Germany

[73] Assignee: Hoechst Aktiengesellschaft, Frankfurt am Main, Fed. Rep. of Germany

[21] Appl. No.: 463,422

[22] Filed: Jan. 11, 1990

[30] Foreign Application Priority Data

Jan. 14, 1989 [DE] Fed. Rep. of Germany ....... 3901000

[51] Int. Cl.$^5$ ....................... C07C 51/58; C07C 59/13
[52] U.S. Cl. ...................................... 562/851; 560/184
[58] Field of Search .......................................... 562/851

[56] References Cited

FOREIGN PATENT DOCUMENTS 203466 12/1986 European Pat. Off. .
2195345 8/1987 Japan .

Primary Examiner—Paul J. Killos

[57] ABSTRACT

A process for the preparation of perfluorinated carbonyl fluorides from hexafluoropropene oxide (HFPO) is described, in which HFPO is oligomerized in an aprotic polar solvent in the presence of a tertiary diamine in the absence or presence of at least one protonic compound. Preferably employed are tetraalkyl-substituted tertiary aliphatic diamine compounds. Protonic compounds which are possibly and preferably used are water, methanol, glycol, ammonia or diethylamine. The selectivity can be displaced in favor of shorter-chain oligomers, in particular of the dimer, by an increased content of these compounds.

14 Claims, No Drawings

PROCESS FOR THE OLIGOMERIZATION OF HEXAFLUOROPROPENE OXIDE

The invention relates to a process for the preparation of oligomers of hexafluoropropene oxide.

The catalyzed oligomerization of hexafluoropropene oxide (HFPO) has been disclosed; the acid fluorides (I) produced during this normally have a wide distribution of molecular masses (n =0-30) (Angew. Chem. (1985) 97, 164).

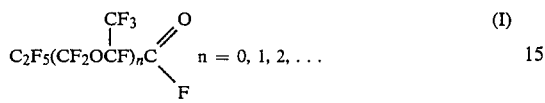

$$n = 0, 1, 2, \ldots \quad (I)$$

Only a few examples of the selective dimerization of HFPO have been disclosed: although an AgNO$_3$/solvent system results in HFPO dimers ((I) with n =1) with a selectivity of 86%, it is, like most silver compounds, light-sensitive and evolves nitrous gases which have to be categorized as a problem (DE-A 20 26 669). The CuCl/CuCl$_2$/acrylonitrile system likewise results in dimeric HFPO with good selectivity, but the toxic acrylonitrile is a great drawback (DE-A 29 24 385). Furthermore, the chlorine content of the catalyst is, undesirably, carried over into the product. In addition, there are strict requirements on constancy of the temperature during the reaction.

Anhydrous manipulation may be assumed to be necessary for the catalyst systems for HFPO oligomerization disclosed in the literature. According to another publication, conventional oligomerization catalysts become selective dimerization catalysts by addition of protonic compounds (JP-A No. 62-195345). However, the cesium fluoride which is exclusively used in the examples represents a catalyst system which is difficult to handle (hygroscopicity) and very costly — especially in view of the fact that some is carried out with the oligomer mixture. It is furthermore to be assumed, on the basis of the cited examples, that for the reaction result it is absolutely necessary to maintain a reaction temperature of minus 20° C, but such a reaction temperature is disadvantageous for industrial application.

It was not possible to repeat the use of the tert. amine/protonic compound system, which is likewise claimed in JP-A No. 62-195345, as selective dimerization catalyst under the stated conditions, especially the preferred conditions. As is shown by Comparative Examples 10 and 11, it was possible to achieve only moderate activity and thus only low conversion. The reacted HFPO mass is recovered in the form of approximately equal parts of dimer ((I), n =1) and—which is usually undesired — monomer ((I), n =0).

Tertiary amines such as triethylamine or N,N-dimethylaniline themselves show only slight oligomerization activity under autogenous pressure (DE-C 1 645 115), and another publication even expressly describes them as inactive (EP-A No. 0 203 466). Active catalysts for the dimerization of HFPO are obtained only with a two-component system composed of N,N-dialkylaniline derivatives or pyridine derivatives, which are not physiologically innocuous, with tetramethylurea.

Hence the object was to eliminate the disadvantages of the catalytic oligomerization of HFPO to and improve the process. The object has been achieved by tertiary diamines of the general formula

$$R^1R^2N-R-NR^3R^4 \quad (II)$$

showing a high catalytic activity in the oligomerization of HFPO in an aprotic polar solvent. This system is able, by specific addition of protonic compounds, selectively to catalyze the dimerization of HFPO.

The invention relates to a process for the preparation of perfluorinated carbonyl fluorides of the general formula

(I)

in which n is equal to zero or an integer from 1 to 8, preferably 1 to 5, by catalyzed oligomerization of hexafluoropropene oxide, in which the hexafluoropropene oxide is oligomerized in an aprotic polar solvent in the presence of a tertiary diamine of the general formula

$$R^1R^2N-R-NR^3R^4 \quad (II)$$

in which R represents an unbranched or branched, saturated or unsaturated hydrocarbon radical which has 1 to 12 carbon atoms and optionally contains at least one hetero chain member or at least one hetero substituent which is inert toward the reaction components, $R^1$ to $R^4$ are, independently of one another, cyclic or acyclic, saturated or unsaturated hydrocarbon radicals which have 1 to 12 carbon atoms and optionally each contain at least one hetero chain member or at least one hetero substituent which is inert toward the reaction components, with, in addition, any two of the radicals $R^1$ to $R^4$ optionally being linked via a hydrocarbon radical or at least one hetero atom, and in the absence or presence of at least one protonic compound. The addition of protonic compounds results in a displacement of the product selectivities in favor of the shorter-chain oligomers (I) (n =0, 1, 2, 3), in particular the dimer (I) (n =1).

Hetero substituents, hetero atoms or hetero chain members are groups which generally contain nitrogen or oxygen as hetero atoms.

The procedure is generally such that initially a diamine is dispersed in an aprotic polar solvent and then — where appropriate after addition of a protonic compound — HFPO is passed in, while stirring and cooling, in such a way that a desired operating pressure is not exceeded. After the reaction is complete, the product phase is separated off and analyzed.

Tertiary diamines of the general formula (II) are easy to obtain (J. Amer. Chem. Soc. (1957) 73, 3518; J. Org. Chem. (1987) 52. 467) and some of them are commercially available.

Example of diamines (II) are tertiary, tetraalkyl-substituted aliphatic diamine compounds having up to 10 carbon atoms in the alkanediyl chain and up to 6 carbon atoms in the alkyl group, as well as heterocyclic diamines, preferably N,N,N',N'-tetramethyl- and -ethylmethylenediamine,
N,N,N',N'-tetramethyl-, -ethyl- and -propylethylenediamine,
N,N,N',N'-tetramethylpropylene-and-isopropylenediamine, N,N,N',N'-tetramethylhexylidenediamine as well as bis(3-methylpiperidino)methane and N,N'-dimethylpiperazine.

Used as diluents are aprotic polar solvents such as aliphatic and aromatic nitriles having 2 to 8 carbon atoms, aliphatic dinitriles having 5-8 carbon atoms and ethers of the formula R'—(O—CH$_2$CHR'')$_x$—OR' in which R' denotes an alkyl group having 1 to 4 carbon atoms, R'' denotes hydrogen or CH$_3$ and x denotes an integer from 1 to 6, as well as cyclic ethers. Nitriles or dinitriles are preferred, such as acetonitrile, propionitrile, butyronitrile, benzonitrile or adiponitrile, as are ethers such as tetrahydrofuran, ethylene and propylene glycol dialkyl ethers and higher oligomers of the latter or mixtures thereof. The aprotic polar solvents can be diluted with inert apolar solvents such as hexane, without this having a detectable effect on the reaction.

The amount of solvent employed is not very crucial.

The amount of diamine (II) employed is between 0.01 and 30 mol-%, preferably between 0.1 and 20 mol-%, relative to the amount of HFPO employed. The catalyst system can be reused after the heavy product phase has been removed; however, this results in a displacement of selectivity in favor of the shorter-chain oligomers.

The catalyst system used in the process according to the invention represents a very active oligomerization catalyst; activities greater than 330 mol mol$^{-1}$h$^{-1}$ can be reached, depending on the pressure maintained and on the temperature.

The oligomerization can be carried out at temperatures from minus 30° to plus 50° C, preferably 5 to 35° C. Low temperatures result in a displacement of selectivity in favor of the higher oligomers (n =2, 3, ...) and lower the conversion of HFPO.

The catalyst system is active even under atmospheric pressure; however, an elevated pressure in the reaction vessel is preferred with a view to more rapid conversion. The pressure in the reaction vessel can be influenced by the rate of inflow of gaseous or liquid HFPO or mixtures thereof.

Protonic compounds which can be employed are substances of the general formula $R^5HX$ (III)

and $R^6R^7R^8N$ (IV)

alone or in a mixture. The meanings in the formulae are: X oxygen or sulfur; $R^5$ hydrogen, alkyl, cycloalkyl, aryl, mono- or polyhydroxyalkyl or -cycloalkyl, mono- or polyhydroxyaryl, mono- or polyaminoalkyl or -cycloalkyl, mono- or polyaminoaryl, mono- or poly(alkylamino)alkyl or -cycloalkyl or mono- or poly(alkylamino)aryl radical; $R^6$ hydrogen, mono- or polyhydroxyalkyl or -cycloalkyl, mono- or polyhydroxyaryl, mono- or polyaminoalkyl or -cycloalkyl, mono- or polyalkylaminoaryl, mono- or poly(alkylamino)alkyl or -cycloalkyl or mono- or poly(alkylamino)aryl radical; $R^7$ and $R^8$ are identical or different and correspond to $R^6$ or an alkyl, cycloalkyl or aryl radical. $R^6$, $R^7$ and $R^8$ can be linked via a carbon chain with or without hetero chain members or via hetero substituents.

Simple protonic additives such as water, methanol, glycol, ammonia, diethylamine or the like are preferred.

The content of protonic compounds in the system used is crucial for the oligomer distribution. As Table 1 shows, taking the example of the N,N,N',N'-tetramethylethylenediamine/acetonitrile/water system, a displacement of selectivity in favor of the shorter-chain oligomers, including the dimer in particular, takes place with increasing content of protonic compounds in the catalyst system. The ratio of the amount of the protonic substance to the diamine (II) depends on the number of active protons. Depending on the intended dimer content, the process can be carried out in the presence of up to 160 mol-%, preferably up to 140 mol-%, of active protons relative to the diamine (II) employed. In this and in the following tables "3+" denotes the content of oligomers with n =3 and above, for example up to n=8.

TABLE 1

Selectivites in % by mass of the HFPO oligomers (I)* as a function of the water content of the catalyst system (CH$_3$)$_2$NCH$_2$CH$_2$N(CH$_3$)$_2$/CH$_3$CN (20-25°; 0.08 bar) in mol % relative to the amount of diamine

| H$_2$O mol % | — | 11 | 22 | 36 | 50 | 64 |
|---|---|---|---|---|---|---|
| n = 0 | 0.4 | 0.8 | 2.5 | 4.9 | 6.6 | 9.4 |
| n = 1 | 27.4 | 54.5 | 75.2 | 80.5 | 86.6 | 85.4 |
| n = 2 | 37.7 | 37.2 | 20.6 | 13.9 | 5.9 | 5.1 |
| n = 3+ | 34.5 | 7.5 | 1.7 | 0.7 | 1.0 | 0.1 |

*analyzed as methyl esters

The advantage of the catalyst used in the process according to the invention is that, on the one hand, it eliminates the difficulties which have been described above and are associated with the state of the art but, on the other hand, it represents a system which is far superior, in terms of oligomerization activity, to the state of the art and is based on simple chemicals which are easy to handle and can be obtained at reasonable price. A further advantage is the flexibility of the process, because one and the said catalyst precursor is used to achieve, on the one hand, an active catalyst system for the formation of higher HFPO oligomers (n =3-5) and, on the other hand, a very active system for the selective dimerization of HFPO after addition of a defined amount of, for example, water as the simplest cocatalyst. A final advantage is the long useful life of the catalyst, associated with a very low solubility of the catalyst species in the product phase, which permits the catalyst system to be employed several times. The apparatus used for the reaction, as well as the substances employed, ought to be substantially free of water in order to rule out hydrolysis and to maintain exact figures on addition of water or other protonic compounds.

Higher HFPO oligomers, in particular the trimer and tetramer of HFPO, are used, for example, as building blocks for perfluorinated inert liquids. The dimer of HFPO is used, inter alia, as intermediate in the preparation of perfluorinated propyl vinyl ether.

EXAMPLES (1) 7.55 ml of dry N,N,N',N'-tetramethylethylenediamine and 50 ml of dry acetonitrile were mixed under protective gas in a reaction vessel provided with a stirrer, internal thermometer and manometer. After gases had been flushed out with HFPO, gaseous HFPO was passed in, while stirring vigorously at 25°-30° C., at a rate such that an operating excess pressure of 2 bar is not exceeded. After 70 minutes, the product phase (110 g) was separated off and analyzed in the form of the methyl esters by gas chromatography. The following oligomer distribution (S =selectivity in % by mass) was found with quantitative conversion:

| $C_2F_5(CF_2OCF)_n COF$ with $CF_3$ branch | | | | | |
|---|---|---|---|---|---|
| (analyzed as methyl esters) | | | | | |
| n | 1 | 2 | 3 | 4 | 5 |
| S (% by mass) | 3.7 | 15.3 | 37.4 | 37.0 | 6.6 |

(2) 7.55 ml of dry N,N,N',N'-tetramethylethylenediamine and 50 ml of dry acetonitrile were mixed in a reaction vessel provided with stirrer, internal thermometer, manometer and a coolable reflux condenser. After gases had been flushed out with HFPO, gaseous HFPO was passed in, while stirring at 25°–30° C., at a rate such that an excess pressure of 0.08 bar was not exceeded. After 4 hours, the product phase (95 g) was separated off and analyzed in the form of the methyl esters by gas chromatography. The following oligomer distribution (in % by mass) was determined at quantitative conversion:

| $C_2F_5(CF_2OCF)_n COF$ with $CF_3$ branch | | | | |
|---|---|---|---|---|
| (analyzed as methyl esters) | | | | |
| n | 0 | 1 | 2 | 3+ |
| S (% by mass) | 0.4 | 27.4 | 37.7 | 34.5 |

(3) 7.55 ml of dry N,N,N',N'-tetramethylethylenediamine, 50 xl of dry acetonitrile and 196 μl water were mixed in the apparatus described in Example 1. After gases had been flushed out with HFPO, gaseous HFPO was passed in, while stirring at 20°–25° C., at a rate such that an operating excess pressure of 2 bar was not exceeded. After 45 minutes, the product phase (103 g) was separated off and analyzed in the form of the methyl esters by gas chromatography. The following oligomer distribution (in % by mass) was found with quantitative conversion:

| $C_2F_5(CF_2OCF)_n COF$ with $CF_3$ branch | | | | |
|---|---|---|---|---|
| (analyzed as methyl esters) | | | | |
| n | 0 | 1 | 2 | 3+ |
| S (% by mass) | 2.0 | 74.2 | 22.1 | 1.7 |

(4) 7.55 ml of dry N,N,N',N'-tetramethylethylenediamine, 50 ml of dry acetonitrile and 196 μl of water were mixed in the apparatus described in Example 2. After gases had been flushed out with HFPO, gaseous HFPO is metered in, while stirring at 20°–25° C., at a rate such that an operating excess pressure of 0.08 bar was not exceeded. After 100 minutes, the product phase (96 g) was separated off and analyzed in the form of the methyl esters by gas chromatography. The following oligomer distribution (in % by mass) was determined at quantitative conversion:

| $C_2F_5(CF_2OCF)_n COF$ with $CF_3$ branch | | | | |
|---|---|---|---|---|
| (analyzed as methyl esters) | | | | |
| n | 0 | 1 | 2 | 3+ |
| S (% by mass) | 2.5 | 75.2 | 20.6 | 1.7 |

(5)–(9) In accordance with Example 4, various catalyst systems composed of 0.05 mol of dry diamine, 50 ml of dry acetonitrile and 196 μl of water were employed. The oligomer distributions specified in Table 2 were found with quantitative conversion.

TABLE 2

Selectivities in % by mass of HFPO oligomers (I)* for various diamines (solvent: acetonitrile + 196 μl of water)

| Example | Diamine | S (% by mass) | | | |
|---|---|---|---|---|---|
| | | n = 0 | n = 1 | n = 2 | n = 3+ |
| 5 | N,N,N',N'-tetramethyl-methylenediamine | 4.4 | 80.9 | 13.8 | 0.8 |
| 6 | N,N,N',N'-tetraethyl-ethylenediamine | 5.0 | 83.2 | 11.1 | 0.7 |
| 7 | N,N,N',N'-tetramethyl-1,6-hexanediamine | 2.3 | 70.3 | 24.7 | 2.6 |
| 8 | N,N'-dimethyl-1,4-piperazine | 3.2 | 82.2 | 14.1 | 0.6 |
| 9 | bis-(3-methyl)-piperidinomethane | 2.9 | 76.8 | 17.6 | 2.6 |

*analyzed as methyl esters

Comparative Example (10)

7 ml of dry triethylamine, 50 ml of dry acetonitrile and 26 μl of water were mixed in the apparatus described in Example 2. After gases had been flushed out with HFPO, gaseous HFPO was passed in, while stirring, in such a way than an operating pressure of 0.08 bar was not exceeded. The internal temperature falls to minus 25° C. during the passing in at an ambient temperature of 20° C. After about 135 minutes, the product phase (91 g) was separated off and analyzed in the form of the methyl esters by gas chromatography. The following oligomer distribution (in % by mass) was determined at a conversion of about 55%:

|   | CF₃ |   |
|---|---|---|
|   | \| |   |
|   | C₂F₅(CF₂OCF)ₙCOF |   |
|   | (analyzed as methyl esters) |   |

| n | 0 | 1 | 2 |
|---|---|---|---|
| S (% by mass) | 50.9 | 49.1 | — |

Comparative Example (11)

The process was carried out as in Example 10, but the reaction was started at minus 20° C. While the HFPO is being passed in the temperature falls to minus 24° C., although the reaction vessel was heated from outside. After 140 minutes, the product phase (91 g) was separated off and analyzed in the form of the methyl esters by gas chromatography. The following oligomer distribution (in % by mass) was determined at a conversion of about 20%.

|   | CF₃ |   |
|---|---|---|
|   | \| |   |
|   | C₂F₅(CF₂OCF)ₙCOF |   |
|   | (analyzed as methyl esters) |   |

| n | 0 | 1 | 2 |
|---|---|---|---|
| S (% by mass) | 50 | 50 | — |

(12) A catalyst system composed of 7.55 ml of dry N,N,N',N'-tetramethylethylenediamine, 50 ml of dry acetonitrile and 882 µl of dry methanol was employed for the HFPO oligomerization in accordance with Example 4. After 150 minutes, the product phase (113 g) was separated off and analyzed in the form of the methyl esters by gas chromatography. The following oligomer distribution was found with complete conversion:

|   | CF₃ |   |   |
|---|---|---|---|
|   | \| |   |   |
|   | C₂F₅(CF₂OCF)ₙCOF |   |   |
|   | (analyzed as methyl esters) |   |   |

| n | 0 | 1 | 2 | 3+ |
|---|---|---|---|---|
| S (% by mass) | 2.3 | 70.6 | 24.5 | 2.6 |

(13) A catalyst system composed of 7.55 ml of dry N,N,N',N'-tetramethylethylenediamine, 50 ml of dry acetonitrile and 1 ml of dry aniline was employed for the HFPO oligomerization in accordance with Example 4. The following oligomer distribution (in % by mass) was found for the product phase (89 g) with complete conversion:

|   | CF₃ |   |   |
|---|---|---|---|
|   | \| |   |   |
|   | C₂F₅(CF₂OCF)ₙCOF |   |   |
|   | (analyzed as methyl esters) |   |   |

| n | 0 | 1 | 2 | 3+ |
|---|---|---|---|---|
| S (% by mass) | 2.3 | 69.5 | 25.1 | 3.1 |

(14) A catalyst system composed of 0.31 ml of dry N,N,N',N'-tetramethylethylenediamine and 50 ml of dry acetonitrile was employed for the HFPO oligomerization in accordance with Example 3. After 40 minutes, the product phase (94 g) was separated off and analyzed in the form of the methyl esters by gas chromatography. The following oligomer distribution was found with quantitative conversion:

|   | CF₃ |   |   |
|---|---|---|---|
|   | \| |   |   |
|   | C₂F₅(CF₂OCF)ₙCOF |   |   |
|   | (analyzed as methyl esters) |   |   |

| n | 0 | 1 | 2 | 3+ |
|---|---|---|---|---|
| S (% by mass) | 0.5 | 30.2 | 45.2 | 3.6 |

(15) Example 4 was repeated replacing the acetonitrile by tetrahydrofuran. After 140 minutes, the product phase (86 g) was separated off and analyzed in the form of the methyl esters by gas chromatography. The following oligomer distribution (in % by mass) was determined at 99% conversion:

|   | CF₃ |   |   |
|---|---|---|---|
|   | \| |   |   |
|   | C₂F₅(CF₂OCF)ₙCOF |   |   |
|   | (analyzed as methyl esters) |   |   |

| n | 0 | 1 | 2 | 3+ |
|---|---|---|---|---|
| S (% by mass) | 4.1 | 60.3 | 28.0 | 7.6 |

(16) 65.4 ml of dry N,N,N',N'-tetramethylethylenediamine, 433 ml of dry acetonitrile and 1.39 ml of water were mixed in a reaction vessel provided with stirrer, internal thermometer, manometer and a coolable reflux condenser. After gases had been flushed out with HFPO, gaseous HFPO was passed in, while stirring at 20°–25° C., at such a rate that an excess pressure of 0.08 bar was not exceeded. After the reaction was complete, the product phase was separated off and then HFPO was passed in again. This process can be repeated several times. Table 3 shows by way of example the oligomer distribution of various oligomer batches prepared with the same catalyst mixture.

TABLE 3

Selectivites in % by mass of HFPO oligomers (I)*
in various batches prepared with the same catalyst system

| Batch | m kg | m (total) kg | Select. in % by mass | | | |
|---|---|---|---|---|---|---|
|   |   |   | n = 0 | n = 1 | n = 2 | n = 3+ |
| 1 | 0.46 | 0.46 | 2.0 | 74.9 | 21.0 | 2.1 |
| 4 | 0.32 | 1.43 | 3.4 | 81.6 | 14.2 | 0.8 |
| 6 | 0.45 | 2.39 | 3.8 | 83.7 | 11.7 | 0.8 |

*analyzed as methyl esters
m = mass of oligomers (I) in the particular batch

I claim:

1. A process for the preparation of perfluorinated carbonyl fluorides of the general formula

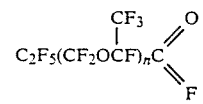

in which n is equal to zero or an integer from 1 to 8, by catalyzed oligomerization of hexafluoropropene oxide, which comprises oligomerization of hexafluoropropene oxide in an aprotic polar solvent in the presence of a tertiary diamine of the general formula $$R^1R^2N-R-NR^3R^4 \qquad (II)$$

in which R represents an unbranched or branched, saturated or unsaturated hydrocarbon radical which has 1 to 12 carbon atoms, $R^1$ to $R^4$ are, independently of one another, cyclic or acyclic, saturated or unsaturated hydrocarbon radicals which have 1 to 12 carbon atoms, and in the absence or presence of at least one protonic compound.

2. The process as claimed in claim 1, wherein R or $R^1$ to $R^4$ each contain at least one hetero chain member or at least one hetero substituent which is inert toward the reaction components.

3. The process as claimed in claim 1, wherein in addition, any two of the radicals $R^1$ to $R^4$ are linked via a hydrocarbon radical or at least one hetero atom.

4. The process as claimed in claim 1, in which at least one protonic compound of the general formulae $$R^5XH \qquad (III)$$
and
$$R^6R^7R^8N \qquad (IV)$$

is used, where the meanings in the formulae are X oxygen or sulfur; $R^5$ hydrogen, alkyl, cycloalkyl, aryl, mono- or polyhydroxyalkyl or -cycloalkyl, mono- or polyhydroxyaryl, mono- or polyaminoalkyl or -cycloalkyl, mono- or polyaminoaryl, mono- or poly(alkylamino)alkyl or -cycloalkyl or mono- or poly(alkylamino)aryl radical; $R^6$ hydrogen, mono- or polyhydroxyalkyl or -cycloalkyl, mono- or polyhydroxyaryl, mono- or polyaminoalkyl or -cycloalkyl, mono- or polyalkylaminoaryl, mono- or poly(alkylamino)alkyl or -cycloalkyl or mono- or poly(alkylamino)aryl radical; $R^7$ and $R^8$ are identical or different and correspond to $R^6$ or an alkyl, cycloalkyl or aryl radical.

5. The process as claimed in claim 4, wherein $R^6$, $R^7$ and $R^8$ are linked via a carbon chain with or without hetero chain members.

6. The process as claimed in claim 1, wherein no protonic compound is added.

7. The process as claimed in claim 1, which is carried out in the presence of 1 to 140 mol-% of protonic compound relative to the diamine employed.

8. The process as claimed in claim 1, wherein water, methanol, glycol, ammonia or diethylamine is used as protonic compound.

9. The process as claimed in claim 1, wherein an aliphatic or aromatic nitrile having 2 to 8 carbon atoms, an aliphatic dinitrile having 5 to 8 carbon atoms, an ether of the formula $$R'-(O-CH_2CHR'')_xOR'$$

in which R' denotes an alkyl group having 1 to 4 carbon atoms, R" denotes hydrogen or $CH_3$ and x denotes an integer from 1 to 6, or a cyclic ether, is used as aprotic polar solvent.

10. The process as claimed in claim 1, wherein the oligomerization is carried out at minus 30° to plus 50° C.

11. The process as claimed in claim 10, wherein the temperature is 5° to 35° C.

12. The process as claimed in claim 1, wherein the amount of diamine (II) employed is 0.01 to 30 mol-% relative to the HFPO employed.

13. The process as claimed in claim 12, wherein the amount of diamine (II) is 0.1 to 20 mol-%.

14. The process as claimed in claim 1, wherein oxygen or nitrogen is present as hetero atom, hetero substituent or hetero chain member.

* * * * *

UNITED STATES PATENT AND TRADEMARK OFFICE
CERTIFICATE OF CORRECTION

PATENT NO.  : 4,973,748
DATED       : 11/27/90
INVENTOR(S) : HEINZ STRUTZ

It is certified that error appears in the above-identified patent and that said Letters Patent is hereby corrected as shown below:

At column 3, line 43, "$R^5HX$" should read -- $R^5XH$ -- .

In claim 1, column 8, line 65

"$C_2F_5(CF_2OCF)_nC\overset{CF_3}{\underset{}{}}\begin{smallmatrix}\diagup O\\ \diagdown F\end{smallmatrix}$"    should read -- $C_2F_5(CF_2OCF)_nC\overset{CF_3}{\underset{}{}}\begin{smallmatrix}\diagup O\\ \diagdown F\end{smallmatrix}$ --

Signed and Sealed this

Fourteenth Day of July, 1992

Attest:

DOUGLAS B. COMER

*Attesting Officer*              Acting Commissioner of Patents and Trademarks